(12) United States Patent
Aseeva et al.

(10) Patent No.: US 8,557,578 B2
(45) Date of Patent: Oct. 15, 2013

(54) EXPANSION MEDIUM FOR CD34-NEGATIVE STEM CELLS

(75) Inventors: Elena Aseeva, Munich (DE); Christine Günther, Munich (DE)

(73) Assignee: Apceth GmbH & Co. KG, Munich (DE)

( * ) Notice: Subject to any disclaimer, the term of this patent is extended or adjusted under 35 U.S.C. 154(b) by 0 days.

(21) Appl. No.: 12/976,333

(22) Filed: Dec. 22, 2010

(65) Prior Publication Data

US 2011/0183414 A1 Jul. 28, 2011

Related U.S. Application Data

(60) Provisional application No. 61/289,796, filed on Dec. 23, 2009.

(51) Int. Cl.
*A61K 35/12* (2006.01)
*A61K 38/00* (2006.01)

(52) U.S. Cl.
USPC ........................................... 435/366; 435/325

(58) Field of Classification Search
USPC ................................................ 435/366, 325
See application file for complete search history.

(56) References Cited

U.S. PATENT DOCUMENTS 7,662,411 B2 *   2/2010   Viswanathan et al. ......... 424/530
2001/0005506 A1 *   6/2001   Cezayirli et al. .............. 424/93.7

OTHER PUBLICATIONS

Schallmoser et al. (Human platelet lysate can replace fetal bovine serum for clinical-scale expansion of functional mesenchymal stromal cells. Transfusion 2007 vol. 47 1436-1446).*
Muller et al. (Secretion of angiogenic proteins by human multipotent mesenchymal stromal cells and their clinical potential in the treatment of avascular osteonecrosis. 2008. Leukemia 22, 2054-2061).*
Muller et al. (Animal serum-free culture conditions for isolation and expansion of multipotent mesenchymal stromal cells from human BM. Cytotherapy. 2006. 8(5) 437-444).*
Koerner et al. (Deep Frozen fresh plasma in blood component therapy: preparation-quality control-indications. Infusionsther Klin Ernahr Oct. 1981 8(5):253-8).*
Schallmoser et al., "Human Platelet Lysate can Replace Fetal Bovine Serum for Clinical-Scale Expansion of Functional Mesenchymal Stromal Cells", Transfusion, American Association of Blood Banks, vol. 47, Aug. 2007, Nr: 8., pp. 1436-1446.
Bernardo et al., "Optimization of in Vitro Expansion of Human Mulitpotent Mesenchymal Stromal Cells for Cell-Therapy Approaches: Further Insights in the Search for a Fetal Calf Serum Substitute", Journal of Cellular Physiology, vol. 211, Dec. 22, 2006, Nr:1, pp. 121-130.
Capelli et al., "Human Platelet Lysate Allows Expansion and Clinical Grade Production of Mesenchymal Stromal Cells from Small Samples of Bone Marrow Aspirates of Marrow Filter Washouts", vol. 40, Aug. 6, 2007, Nr: 8, pp. 785-791.
Johansson et al., "Platelet Lysate: a Replacement for Fetal Bovine Serum in Animal Cell Culture?", Cytotechnology, vol. 42, Jul. 2006, Nr. 2, pp. 67-74.
Blande et al., "Adipose Tissue Mesenchymal Stem Cell Expansion in Animal Serum-Free Medium Supplemented with Autologous Human Platelet Lysate", Transfusion, vol. 49, Dec. 2009, pp. 2680-2685.
Horn et al., "Impact of Individual Platelet Lysates on Isolation and Growth of Human Mesenchymal Stromal Cells", Cytotherapy, 2010, 12:888-898.
Kocaoemer et al., "Human AB Serum and Thrombin-Activated Platelet-Rich Plasma are Suitable Alternatives to Fetal Calf Serum for the Expansion of Mesenchymal Stem Cells from Adipose Tissue", Stem Cells, Nov. 11, 2008, pp. 1271-1278.
Langer and Gawaz, "Platelets in Regenerative Medicine", Basic Res Cardiol, 2008, 103:299-307.
Salvadé et al, "Characterization of Platelet Lysate Cultured Mesenchymal Stromal Cells and Their Potential Use in Tissue-Engineered Osteogenic Devices for the Treatment of Bone Defects," Tissue Eng Part C Methods, 15, 2009:185-196.
Schallmoser et al., "Rapid Large-Scale Expansion of Functional Mesenchymal Stem Cells from Unmanipulated Bone Marrow Without Animal Serum", Tissue Eng part C. Methods, 14(3):185-96.
Stellos and Gawaz, "Platelet Interaction with Progenitor Cells: Potential Implications for Regenerative Medicine", Thromb Haemost, 2007, 98:922-929.

* cited by examiner

*Primary Examiner* — Karen Cochrane Carlson
*Assistant Examiner* — Natalie Moss
(74) *Attorney, Agent, or Firm* — Cozen O'Connor

(57) ABSTRACT

This invention provides a cell growth medium comprising (a) a human platelet lysate free of solid matter greater than 0.22 μm in diameter, wherein the lysate constitutes from 2% to 15% of the total volume of the cell growth medium; (b) a human fresh frozen plasma (FFP) filtrate free of solid matter greater than 0.22 μm in diameter, wherein the FFP filtrate constitutes from 1% to 10% of the total volume of the cell growth medium; (c) heparin at a concentration of from 0 U/ml to 10 U/ml of the cell growth medium; (d) L-glutamine at a concentration of from 0.5 mM to 10 mM; and (e) a serum-free, low glucose medium suitable for mammalian cell growth, wherein the serum-free, low glucose medium constitutes from 75% to 97% of the total volume of the cell growth medium, and may contain the L-glutamine of part (d); wherein the cell growth medium permits the expansion of human CD34⁻ stem cells and wherein the resulting expanded CD34⁻ stem cells retain the ability to differentiate. This invention also provides related cell growth medium supplements, a sterile human platelet lysate and human fresh frozen plasma (FFP) filtrate, kits, CD34⁻ stem cell-containing compositions, and related production and cell expansion methods.

19 Claims, 14 Drawing Sheets

Doubling time of MSCs in media of different compositions

Proliferation rate of MSC in different media

Dynamics of MSC-growth in Bio-1

Expression of MSC-specific surface proteins

Analysis of MSC population by flow cytometry

Induced differentiation of MSCs growth in Bio-1

Doubling time (days) of MSCs

| Sample: | 1 | 2 | 3 | 4 | 5 | 6 |
|---|---|---|---|---|---|---|
| | TK + FFP 4000g | TK + FFP 4000g + 100μm | TK + FFP 100 μm | TK + FFP 40 μm | TK + FFP 40 μm + 0.22μm | TK + FFP 40 μm + 0.4 μm |
| P1 | 2.32 | 2.35 | 2.15 | 1.55 | 1.58 | 1.52 |
| P2 | | | | 1.6 | 1.52 | 1.56 |

Amount of doublings achieved after 12 days

| Sample: | 1 | 2 | 3 | 4 | 5 | 6 |
|---|---|---|---|---|---|---|
| | TK + FFP 4000g | TK + FFP 4000g + 100μm | TK + FFP 100 μm | TK + FFP 40 μm | TK + FFP 40 μm + 0.22μm | TK + FFP 40 μm + 0.4 μm |
| | 5.17 | 4.25 | 5.58 | 7.59 | 7.79 | 7.76 |

Doubling time (days) of MSCs

| TK + FFP 4000xg | TK + FFP 40 μm | TK + FFP 40 μm, 0.45 μm | TK + FFP 4000xg, 40μm, 0.45μm | TK 0.45μm +FFP 4000xg | TK 0.45μm +FFP 40μm | TK 0.45μm +FFP 40μm, 0.45μm | TK 0.45μm +FFP 4000xg, 40μm, 0.45μm |
|---|---|---|---|---|---|---|---|
| 8.12 | | 9.28 | 10.32 | 4.03 | 4.64 | 3.98 | 3.63 |

EXPANSION MEDIUM FOR CD34-NEGATIVE STEM CELLS

This application claims priority of U.S. Provisional Application No. 61/289,796, filed Dec. 23, 2009, the contents of which are incorporated herein by reference in their entirety.

Throughout this application, various publications are cited. The disclosure of these publications is hereby incorporated by reference into this application to describe more fully the state of the art to which this invention pertains.

BACKGROUND OF THE INVENTION

Human non-hematopoetic stem cells originating from the bone marrow and cord blood are increasingly used as mesenchyrnal cells for regenerative and immunemodulatory indications in patients. More than 80 clinical trials have been performed world-wide with mesenchymal stem cells.

Nearly all investigators use fetal bovine serum (FBS)-containing media as the standard serum supplement. FBS is of bovine origin, may transmit TSE (i.e., Transmissible Spongiform Encephalopathy) and stimulates immune responses in the recipient. Only BSE-free cattle are licensed by the authorities for use in humans (New Zealand) and investigators are engaged in efforts to develop alternative approaches for promoting cell growth. As cell-based therapies will likely be increasingly used in coming years, there will be an accompanying shortage of FBS.

Some companies have developed serum-free media. However, these media exhibit lower than ideal growth rates, and the morphology and the properties of bone marrow-derived CD34-negative stem cells in these media are not characterized as extensively as those in FBS-containing media.

Human thrombocytes (i.e., platelets) have been used by other investigators, as has Fresh Frozen Plasma (FFP), as growth-enhancing components. Platelets and their potential implications for regenerative medicine are reviewed separately by Stellos and Gawaz, and by Langer and Gawaz.

The following specific teachings in the art are noted with respect to stem cell expansion using platelets or FFP. Schallmoser, et al. discloses mesenchymal stem cell expansion using platelet lysate. Capelli, et al. discloses the use of non-filtered human platelet lysate to expand and produce mesenchymal stromal cells. Kocaoemer, et al. discloses the use of human AB serum and thrombin-activated platelet-rich plasma in expanding mesenchymal stem cells from adipose tissue. Muller, et al. discloses animal serum-free culture conditions for isolating and expanding multipotent mesenchymal stromal cells from human bone marrow, where these conditions employ both FFP and platelets. Blande, et al. discloses adipose tissue mesenchymal stem cell expansion in animal serum-free medium supplemented with autologous human platelet lysate that has been sterile filtered. Likewise, Salvadè, et al. discloses the use of platelet lysate in culturing mesenchymal stromal cells, wherein the lysate is sterile filtered.

Despite the known use of platelet lysate and FFP in culturing mesenchymal stem cells, there still exists an unmet need for a more rapid, cost-effective and safe way to culture such cells in a stable manner while preserving their ability to differentiate later when desired.

SUMMARY OF THE INVENTION

This invention provides a cell growth medium comprising
(a) a human platelet lysate free of solid matter greater than 0.22 μm in diameter, wherein the lysate constitutes from 2% to 15% of the total volume of the cell growth medium;
(b) a human fresh frozen plasma (FFP) filtrate free of solid matter greater than 0.22 μm in diameter, wherein the FFP filtrate constitutes from 1% to 10% of the total volume of the cell growth medium;
(c) heparin at a concentration of from 0 U/ml to 10 U/ml of the cell growth medium;
(d) L-glutamine at a concentration of from 0.5 mM to 10 mM; and
(e) a serum-free, low glucose medium suitable for mammalian cell growth, wherein the serum-free, low glucose medium constitutes from 75% to 97% of the total volume of the cell growth medium, and may contain the L-glutamine of part (d);

wherein the cell growth medium permits the expansion of human CD34⁻ stem cells and wherein the resulting expanded CD34⁻ stem cells retain the ability to differentiate.

This invention also provides a cell growth medium supplement comprising
(a) human platelet lysate free of solid matter greater than 0.22 μm in diameter, wherein the lysate constitutes from 17% to 94% of the total volume of the cell growth medium supplement; and
(b) human fresh frozen plasma (FFP) filtrate free of solid matter greater than 0.22 μm in diameter, wherein the FFP filtrate constitutes from 6% to 83% of the total volume of the cell growth medium supplement;

wherein when the cell growth medium supplement is combined with heparin and an L-glutamine-containing, serum-free, low glucose medium suitable for mammalian cell growth, in order to form a cell growth medium containing (i) 3% to 25% by volume of the cell growth medium supplement, (ii) heparin at a concentration of from 0 U/ml to 10 U/ml, and (iii) L-glutamine at a concentration of from 0.5 mM to 10 mM, the resulting cell growth medium permits the expansion of human CD34⁻ stem cells and the resulting expanded CD34⁻ stem cells retain the ability to differentiate.

This invention further provides a human platelet lysate free of solid matter greater than 0.22 μm in diameter, wherein the platelet lysate is prepared according to the following steps:
(i) freezing platelet concentrate, thereby lysing the platelets therein;
(ii) thawing the resulting lysed platelets;
(iii) centrifuging the thawed lysed platelets at a speed and for a duration suitable to pellet solid matter therein;
(iv) re-centrifuging the supernatant from step (iii) at a speed and for a duration suitable to pellet solid matter therein; and
(v) filtering the supernatant from step (iv) at least twice using filters of decreasing pore size, wherein the first filtration is performed using a filter having pores of at least 5 μm, and the last filtration is performed using a filter having pores no larger than 0.22 μm.

This invention still further provides a human fresh frozen plasma (FFP) filtrate free of solid matter greater than 0.22 μm in diameter, wherein the FFP filtrate is prepared according to the following steps:
(i) thawing FFP;
(ii) centrifuging the thawed FFP at a speed and for a duration suitable to separate the liquid and solid portions thereof; and
(iii) filtering the resulting liquid portion at least twice using filters of decreasing pore size, wherein the first filtration is performed using a filter having pores of at least 5 μm, and the last filtration is performed using a filter having pores no larger than 0.22 μm.

Also provided is a kit for use in expanding human CD34⁻ stem cells comprising, in separate compartments, (a) a human platelet lysate free of solid matter greater than 0.22 μm in diameter, and
(b) a human fresh frozen plasma (FFP) filtrate free of solid matter greater than 0.22 μm in diameter,
  wherein (i) the lysate constitutes from 17% to 94% of the combined volume of (a) and (b), (ii) the FFP filtrate constitutes from 6% to 83% of the combined volume of (a) and (b), and (iii) when the lysate and filtrate are combined with heparin and with L-glutamine-containing, serum-free, low glucose medium suitable for mammalian cell growth, in order to form a cell growth medium wherein (i) the kit's contents constitute 3% to 25% of the medium by volume and (ii) heparin is at a concentration of from 0 U/ml to 10 U/ml, the resulting cell growth medium permits the expansion of human $CD34^-$ stem cells and the resulting expanded $CD34^-$ stem cells retain the ability to differentiate.

This invention also provides a composition of matter comprising (a) human $CD34^-$ stem cells and (b) the any of the embodiments of the subject cell growth medium.

This invention further provides a method for making a human platelet lysate free of solid matter greater than 0.22 μm in diameter, comprising the following steps:
(i) freezing platelet concentrate, thereby lysing the platelets therein;
(ii) thawing the resulting lysed platelets;
(iii) centrifuging the thawed lysed platelets at a speed and for a duration suitable to pellet solid matter therein;
(iv) re-centrifuging the supernatant from step (iii) at a speed and for a duration suitable to pellet solid matter therein; and
(v) filtering the supernatant from step (iv) at least twice using filters of decreasing pore size, wherein the first filtration is performed using a filter having pores of at least 5 μm, and the last filtration is performed using a filter having pores no larger than 0.22 μm.

This invention still further provides a method for making a human fresh frozen plasma (FFP) filtrate free of solid matter greater than 0.22 μm in diameter, comprising the following steps:
(i) thawing FFP;
(ii) centrifuging the thawed FFP at a speed and for a duration suitable to separate the liquid and solid portions thereof; and
(iii) filtering the resulting liquid portion at least twice using filters of decreasing pore size, wherein the first filtration is performed using a filter having pores of at least 5 μm, and the last filtration is performed using a filter having pores no larger than 0.22 μm.

This invention also provides a method for making a cell growth medium comprising the step of combining the following:
(a) a human platelet lysate free of solid matter greater than 0.22 μm in diameter, wherein the lysate constitutes from 2% to 15% of the total volume of the cell growth medium;
(b) a human fresh frozen plasma (FFP) filtrate free of solid matter greater than 0.22 μm in diameter, wherein the FFP filtrate constitutes from 1% to 10% of the total volume of the cell growth medium;
(c) heparin in an amount sufficient to yield a concentration of from 0 U/ml to 10 U/ml of the cell growth medium;
(d) L-glutamine in an amount sufficient to yield a concentration of from 0.5 mM to 10 mM; and
(e) a serum-free, low glucose medium suitable for mammalian cell growth, wherein the serum-free, low glucose medium constitutes from 75% to 97% of the total volume of the cell growth medium, and may contain the L-glutamine of part (d);

wherein the cell growth medium permits the expansion of human $CD34^-$ stem cells and wherein the resulting expanded $CD34^-$ stem cells retain the ability to differentiate.

This invention provides a method for expanding a population of human $CD34^-$ stem cells comprising the step of incubating the stem cells at a suitable temperature in the subject cell growth medium.

This invention also provides a human $CD34^-$ stem cell (i) having the ability to differentiate, and (ii) resulting from an expansion of a population of human $CD34^-$ stem cells, wherein the expansion comprises incubating the population of stem cells at a suitable temperature in the subject cell growth medium.

Finally, this invention provides a population of human $CD34^-$ stem cells (i) having the ability to differentiate, and (ii) resulting from an expansion of a population of human $CD34^-$ stem cells, wherein the expansion comprises incubating the population of stem cells at a suitable temperature in the subject cell growth medium.

Figure 1:
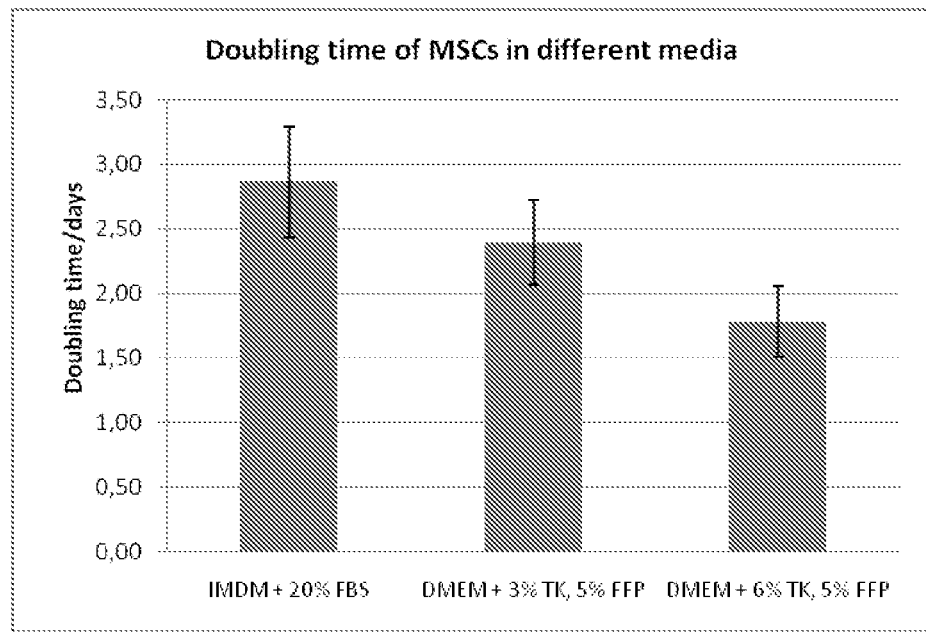
FIG. 1
Doubling time of MSCs in media of different compositions.

Control of MSC growth with different TK and FFP preparations. TK and FFP were subjected to different filtration steps. Microscopic photographs show the cell growth after 7 days of cultivation. The medium prepared with TK and FFP both filtered via 40 μm and 0.20 μm filters provided the most efficient MSC growth (sample 2), also when the resulting medium was filtered via 0.20 μm again (sample 5). In all cases, cell growth was sufficiently promoted.

FIG. 13

Analysis of CD41$^+$ in MSCs grown in Bio-1 prepared with different filtration steps. MSCs from donors AP00029, AP00042 and AP00045 were used for the analysis. (A) 1—control; 2—TK 0.8 μm/0.2 μm+FFP; 3—TK+FFP 0.8 μm/0.2 μm; 4—Tk 0.8 μm/0.2 μm+FFP 0.8 μm/0.2 μm. (B) 1—control; 2—TK 8 μm+FFP; 3—TK+FFP 8 μm; 4—TK 8 μm+FFP 8 μm. (C) 1—control; 2—TK 8 μm/0.8 μm/0.2 μm+FFP; 3—TK+FFP 8 μm/0.8 μm/0.2 μm; 4—TK 8 μm/0.2 μm+FFP 8 μm/0.8 μm/0.2 μm. (D) 1—control; 2—TK 0.8 μm/0.2 μm+FFP 0.8 μm/0.2 μm+Bio-1 0.8 μm/0.2 μm; 3—TK 8 μm/0.8 μm/0.2 μm+FFP 8 μm/0.8 μm/0.2 μm+Bio-1 0.8 μm/0.2 μm.

FIG. 14

Analysis of MSC growth in Bio-1 with (1) standard FFP and (2) cryoprecipitate-free FFP.

DETAILED DESCRIPTION OF THE INVENTION

This invention provides a novel growth medium that permits the unexpectedly rapid expansion of human CD34$^-$ stem cells. The expanded stem cells do not differentiate until otherwise induced to do so, however. Thus, the growth medium of this invention, and its related methods, constitute a significant improvement in the ability to rapidly, safely and inexpensively generate clinically significant numbers of CD34$^-$ stem cells for use in treating disease.

Specifically, this invention provides a cell growth medium comprising
(a) a human platelet (i.e., thrombocyte) lysate free of solid matter greater than 0.22 μm in diameter, wherein the lysate constitutes from 2% to 15% of the total volume of the cell growth medium;
(b) a human fresh frozen plasma (FFP) filtrate free of solid matter greater than 0.22 μm in diameter, wherein the FFP filtrate constitutes from 1% to 10% of the total volume of the cell growth medium;
(c) heparin at a concentration of from 0 U/ml to 10 U/ml of the cell growth medium;
(d) L-glutamine at a concentration of from 0.5 mM to 10 mM; and
(e) a serum-free, low glucose medium suitable for mammalian cell growth, wherein the serum-free, low glucose medium constitutes from 75% to 97% of the total volume of the cell growth medium, and may contain the L-glutamine of part (d);
wherein the cell growth medium permits the expansion of human CD34$^-$ stem cells and wherein the resulting expanded CD34$^-$ stem cells retain the ability to differentiate.

The following are among the preferred embodiments of this cell growth medium: (i) the lysate constitutes from 3% to 8%, from 5% to 7%, and preferably 6%, of the total volume of the cell growth medium; (ii) the FFP filtrate constitutes from 2% to 7%, from 4% to 6%, and preferably 5%, of the total volume of the cell growth medium; (iii) heparin is at a concentration of from 0.8 U/ml to 1.2 U/ml, and preferably 1 U/ml, of the cell growth medium; (iv) L-glutamine is at a concentration of from 0.5 mM to 10 mM, and preferably 2 mM; and (v) the serum-free, low glucose (1 mg/ml) medium is L-glutamine-containing, low glucose DMEM (Dulbecco's Modified Eagle Medium) and constitutes from 85% to 93%, from 87% to 91%, and preferably 89%, of the total volume of the cell growth medium.

In a further preferred embodiment, the expanded CD34$^-$ stem cells have the phenotype CD34$^-$/CD45$^-$/CD73$^+$/CD105$^+$/CD90$^+$. By this phenotype, it is meant that markers CD34 and CD45 appear on 0%±10% (and preferably ±0.5%) of expanded cells upon testing for such markers (using, for example, flow cytometric analysis). Likewise, markers CD73, CD105 and CD90 appear on 100%±10% (and preferably ±0.5%) of expanded cells upon testing for such markers.

As used herein, "CD34$^-$ stem cell" shall mean a stem cell lacking CD34 on its surface. CD34$^-$ stem cells can be derived from tissues such as bone, umbilical cord and adipose tissue, for example. CD34$^-$ stem cells, and methods for isolating same, are described, for example, in Lange C. et al., Accelerated and safe expansion of human mesenchymal stromal cells in animal serum-free medium for transplantation and regenerative medicine. *J. Cell Physiol.* 2007, Apr. 25 [Epub ahead of print].

In one embodiment of the invention, the term fresh frozen plasma (FFP) refers to the liquid portion of human blood that has been frozen and preserved. In particular, the term FFP, in an embodiment, refers to the fluid portion of human blood that has been centrifuged, separated, and frozen solid at −18° C. within 6 hours of collection.

The serum-free, low glucose medium suitable for mammalian cell growth can comprise, for example, various amino acids, vitamins, salts and other compounds. In the preferred embodiment of the invention, the serum-free, low glucose medium is (DMEM) low in glucose, which may also include L-glutamine. Provided below in Tables 1 and 2, as examples, are two nearly identical growth medium formulations.

TABLE 1

Dulbecco's Modified Eagle Medium (DMEM) Low Glucose
DMEM contains, mg/ml:

Inorganic salts:

0.0002 mg CaCl
0.0001 mg Fe(NO$_3$)$_3$ × 9 H$_2$O
0.0004 mg KCl
0.0000977 mg MgSO$_4$
0.0064 mg NaCl
0.000125 mg NaH$_2$PO$_4$ × 2 H$_2$O
0.0037 mg NaHCO$_3$

Amino acids:

0.000084 mg L-Arginine × HCl
0.000048 mg L-Cystine
0.005584 mg L-Glutamine
0.000030 mg Glycine
0.000042 mg L-Histidine × HCl × H$_2$O
0.000105 mg L-Isoleucine
0.000105 mg L-Leucine
0.000146 mg L-Lysine × HCl
0.00003 mg L-Methionine
0.000066 mg L-Phenylalanine
0.000042 mg L-Serine
0.000095 mg L-Threonine
0.000016 mg L-Tryptophan TABLE 1-continued Dulbecco's Modified Eagle Medium (DMEM) Low Glucose
DMEM contains, mg/ml:

0.000072 mg L-Tyrosine
0.000094 mg L-Valine
Vitamins:

0.000004 mg D-Calcium-Pantothenate
0.000004 mg Choline chloride
0.000004 mg Folate
0.0000072 mg Myo-Inositol
0.000004 mg Nicotinamide
0.000004 mg Pyridoxal × HCl
0.0000004 mg Riboflavin
0.000004 mg Thiamine × HCl
Other components:

0.001 mg D-Glucose
0.000015 mg Phenol red
0.00011 mg Sodium pyruvate
0.9862567 mg H$_2$O
Water:

0.9862567 mg

TABLE 2

Dulbecco's Modified Eagle Medium, DMEM
Low Glucose
Compound Formula mg/L

| Part A: Inorganic Salts | |
|---|---|
| Calcium chloride (anhydrous) | 200.00 |
| Ferric nitrate | 0.10 |
| Magnesium sulfate | 200.00 |
| Potassium chloride | 400.00 |
| Sodium bicarbonate | 3700.00 |
| Sodium chloride | 6400.00 |
| Sodium phosphate, H$_2$0 | 125.00 |
| Part B: Other components | |
| D-Glucose | 1000.00 |
| Phenol Red | 15.00 |
| Sodium pyruvate | 110.00 |
| Part C: Amino Acids | |
| L-Arginine hydrochloride | 84.00 |
| L-Cystine | 48.00 |
| L-Glutamine | 584.00 |
| Glycine | 30.00 |
| L-Histidine hydrochloride | 42.00 |
| L-Isoleucine | 105.00 |
| L-Leucine | 105.00 |
| L-Lysine HCl | 146.00 |
| L-Methionine | 30.00 |
| L-Phenylalanine | 66.00 |
| L-Serine | 42.00 |
| L-Threonine | 95.00 |
| L-Tryptophan | 16.00 |
| L-Tyrosine | 72.00 |
| L-Valine | 94.00 |
| Part D: Vitamins | |
| D-Calcium pantothenate | 4.00 |
| Choline chloride | 4.00 |
| i-Inositol | 7.20 |
| Nicotinamide | 4.00 |
| Pyridoxine hydrochloride | 4.00 |
| Thiamine hydrochloride | 4.00 |
| Folic acid | 4.00 |
| Riboflavin | 0.40 |

[pH 7.0 Osmolarity: 324-333 mOsm]

Human platelets (i.e., thrombocytes) can be obtained from whole blood or from apheresis. Platelets may be derived from single donor or matched pooled donors. In the preferred embodiment, single-donor apheresis is used. Likewise, FFP can be derived from whole blood or from apheresis. Preferably, apheresis is used to prepare FFP. Platelet concentrate, as well as FFP concentrate, can be prepared according to routine methods, such as those described in "Guide to the preparation, use and quality assurance of blood components", Council of Europe, Recommendation; and "Transfusionsgesetz and Richtlinien zur Hämotherapie" (Germany).

In a preferred embodiment, the platelet unit used has the following characteristics: volume is 200-300 ml; thrombocyte content is $2-4 \times 10^{11}$/unit; erythrocyte content is $<3 \times 10^9$/unit; leukocyte content is $<1 \times 10^6$/unit of platelets; and the donor is negative for HLA-antibodies (important for avoidance of immune complications). These are the characteristics according to the manufacturer's license. Other platelet units may also be used.

In the preferred embodiment of the subject cell growth medium, the platelet lysate of part (a) is prepared according to the following steps:
(i) freezing human platelet concentrate, thereby lysing the platelets therein;
(ii) thawing the resulting lysed platelets;
(iii) centrifuging the thawed lysed platelets at a speed and for a duration suitable to pellet solid matter therein;
(iv) re-centrifuging the supernatant from step (iii) at a speed and for a duration suitable to pellet solid matter therein; and
(v) filtering the supernatant from step (iv) at least twice using filters of decreasing pore size, wherein the first filtration is performed using a filter having pores of at least 5 μm, and the last filtration is performed using a filter having pores no larger than 0.22 μm.

In one embodiment of this invention, filtering step (v) is omitted.

In one embodiment, the human platelet concentrate of step (i) is prepared by: centrifuging platelets and thereby pelleting them; separating the pelleted platelets from the liquid phase; and reconstituting the resulting platelets in FFP.

The following are certain additional preferred embodiments of this process for preparing the platelet lysate: freezing human platelet concentrate is performed at between −20 and −80° C., and preferably at −80° C.; thawing the lysed platelets is performed at between 18 and 37° C., and preferably at 37° C.; centrifuging the thawed lysed platelets is performed at between 9,000×g and 55,000×g, and preferably at 10,000×g, for between 10 and 20 minutes, and preferably 20 minutes; re-centrifuging the supernatant from step (iii) is performed at between 3,000×g and 5,000×g, and preferably at 4,000×g, for 10 minutes; and filtering the supernatant from step (iv) is performed three times using filters of decreasing pore size, namely 40 μm±5 μm, 5 μm±1 μm, and 0.22 μm.

The reconstituted platelets can then be subjected to the above mentioned step (i), the freezing step. Such a procedure can accomplish a good blood group compatibility between the blood group antigens and the isoagglutinins in the plasma. The FFP used to reconstitute the platelets in step (ic) can be prepared according to any of the below described methods.

Also, in the preferred embodiment of the subject cell growth medium, the FFP filtrate of part (b) is prepared according to the following steps:
(i) thawing human FFP;
(ii) centrifuging the thawed FFP at a speed and for a duration suitable to separate the liquid and solid portions thereof; and
(iii) filtering the resulting liquid portion at least twice using filters of decreasing pore size, wherein the first filtration is performed using a filter having pores of at least 5 μm, and the last filtration is performed using a filter having pores no larger than 0.22 μm.

In one embodiment of this invention, filtering step (iii) is omitted.

In another embodiment of this invention, the FFP filtrate of part (b) is prepared by: (i) thawing human FFP; (ii) freezing the thawed human FFP; (iii) thawing the resulting human FFP; and (iv) centrifuging the resulting thawed FFP at a speed and for a duration suitable to separate the liquid and solid portions thereof. Preferably, the thawed FFP from step (iii) is frozen and thawed at least once again before the centrifugation step (iv). Also, in one embodiment, a filtering of the liquid portion resulting from step (iv) is omitted.

The following are certain preferred embodiments of this process for preparing the FFP filtrate: thawing the FFP is performed at between 18 and 37° C., and preferably at 37° C.; centrifuging the thawed FFP is performed at between 9,000×g and 55,000×g, and preferably at 10,000×g, for between 10 and 20 minutes, and preferably 20 minutes; and filtering the liquid portion from step (ii) is performed three times using filters of decreasing pore size, namely 40 μm±5 μm, 5 μm±1 μm, and 0.22 μm.

Ideally, the subject cell growth medium is free of animal serum. This reduces the complications that can arise when introducing non-human antigens into a human subject.

Preferably, in the subject cell growth medium, the platelet lysate and FFP filtrate are matched with respect to blood group antigens ABO and Rh. That is, the platelet lysate and FFP filtrate are preferably derived from subjects having these same blood group antigens (for example, both the lysate and filtrate are derived from $O^+/Rh^+$ subjects). This topic is discussed in more detail below.

This invention also provides a cell growth medium supplement comprising
(a) human platelet lysate free of solid matter greater than 0.22 μm in diameter, wherein the lysate constitutes from 17% to 94% of the total volume of the cell growth medium supplement; and
(b) human fresh frozen plasma (FFP) filtrate free of solid matter greater than 0.22 μm in diameter, wherein the FFP filtrate constitutes from 6% to 83% of the total volume of the cell growth medium supplement;
wherein when the cell growth medium supplement is combined with heparin and an L-glutamine-containing, serum-free, low glucose medium suitable for mammalian cell growth, in order to form a cell growth medium containing (i) 3% to 25% by volume of the cell growth medium supplement, (ii) heparin at a concentration of from 0 U/ml to 10 U/ml, and (iii) L-glutamine at a concentration of from 0.5 mM to 10 mM, the resulting cell growth medium permits the expansion of human $CD34^-$ stem cells and the resulting expanded $CD34^-$ stem cells retain the ability to differentiate.

This cell growth medium supplement is in fact used as a "concentrate" for addition to a standard growth medium like DMEM. Thus, the supplement preferably yields the preferred concentrations of platelet lysate and FFP filtrate discussed above (e.g., the platelet lysate and FFP filtrate constitute 54.5% and 45.5% of the supplement, respectively).

In one embodiment, the subject cell growth medium supplement further comprises heparin, wherein when the cell growth medium supplement is combined with L-glutamine-containing, serum-free, low glucose medium suitable for mammalian cell growth, in order to form a cell growth medium containing 3% to 25% (and preferably 11%) by volume of the cell growth medium supplement and having from 0 U/ml to 10 U/ml (and preferably 1 U/ml) of heparin, the resulting cell growth medium permits the expansion of human $CD34^-$ stem cells and the resulting expanded $CD34^-$ stem cells retain the ability to differentiate.

Preferably, in the subject cell growth medium supplement, the platelet lysate of part (a) is prepared according to the following steps:
(i) freezing human platelet concentrate, thereby lysing the platelets therein;
(ii) thawing the resulting lysed platelets;
(iii) centrifuging the thawed lysed platelets at a speed and for a duration suitable to pellet solid matter therein;
(iv) re-centrifuging the supernatant from step (iii) at a speed and for a duration suitable to pellet solid matter therein; and
(v) filtering the supernatant from step (iv) at least twice using filters of decreasing pore size, wherein the first filtration is performed using a filter having pores of at least 5 μm, and the last filtration is performed using a filter having pores no larger than 0.22 μm.

In one embodiment of this invention, filtering step (v) is omitted.

Also preferred in the subject cell growth medium supplement, the FFP filtrate of part (b) is prepared according to the following steps:
(i) thawing human FFP;
(ii) centrifuging the thawed FFP at a speed and for a duration suitable to separate the liquid and solid portions thereof; and
(iii) filtering the resulting liquid portion at least twice using filters of decreasing pore size, wherein the first filtration is performed using a filter having pores of at least 5 μm, and the last filtration is performed using a filter having pores no larger than 0.22 μm.

In one embodiment of this invention, filtering step (iii) is omitted.

As with all embodiments of the subject growth medium, the cell growth medium supplement ideally is also free of animal serum.

Also preferred in the subject cell growth medium supplement is where the platelet lysate and FFP filtrate are matched with respect to blood group antigens ABO and Rh. This again is as discussed above regarding the subject growth medium.

This invention further provides a human platelet lysate free of solid matter greater than 0.22 μm in diameter, wherein the platelet lysate is prepared according to the following steps:
(i) freezing human platelet concentrate, thereby lysing the platelets therein;
(ii) thawing the resulting lysed platelets;
(iii) centrifuging the thawed lysed platelets at a speed and for a duration suitable to pellet solid matter therein;
(iv) re-centrifuging the supernatant from step (iii) at a speed and for a duration suitable to pellet solid matter therein; and
(v) filtering the supernatant from step (iv) at least twice using filters of decreasing pore size, wherein the first filtration is performed using a filter having pores of at least 5 μm, and the last filtration is performed using a filter having pores no larger than 0.22 μm.

In one embodiment of this invention, filtering step (v) is omitted.

This invention still further provides a human fresh frozen plasma (FFP) filtrate free of solid matter greater than 0.22 μm in diameter, wherein the FFP filtrate is prepared according to the following steps:
(i) thawing human FFP;
(ii) centrifuging the thawed FFP at a speed and for a duration suitable to separate the liquid and solid portions thereof; and (iii) filtering the resulting liquid portion at least twice using filters of decreasing pore size, wherein the first filtration is performed using a filter having pores of at least 5 μm, and the last filtration is performed using a filter having pores no larger than 0.22 μm.

In one embodiment of this invention, filtering step (iii) is omitted.

Also provided is a kit for use in expanding human CD34⁻ stem cells comprising, in separate compartments,
(a) a human platelet lysate free of solid matter greater than 0.22 μm in diameter, and
(b) a human fresh frozen plasma (FFP) filtrate free of solid matter greater than 0.22 μm in diameter,
wherein (i) the lysate constitutes from 17% to 94% (and preferably 54.5%) of the combined volume of (a) and (b), (ii) the FFP filtrate constitutes from 6% to 83% (and preferably 45.5%) of the combined volume of (a) and (b), and (iii) when the lysate and filtrate are combined with heparin and with L-glutamine-containing, serum-free, low glucose medium suitable for mammalian cell growth, in order to form a cell growth medium wherein (i) the kit's contents constitute 3% to 25% (and preferably 11%) of the medium by volume and (ii) heparin is at a concentration of from 0 U/ml to 10 U/ml (and preferably 1 U/ml), the resulting cell growth medium permits the expansion of human CD34⁻ stem cells and the resulting expanded CD34⁻ stem cells retain the ability to differentiate.

In one embodiment of the subject kit, the kit comprises, in separate compartments,
(a) a human platelet lysate free of solid matter greater than 0.22 μm in diameter,
(b) a human fresh frozen plasma (FFP) filtrate free of solid matter greater than 0.22 μm in diameter, and
(c) heparin,
wherein (i) the lysate constitutes from 17% to 94% (and preferably 54.5%) of the combined volume of (a)-(c), (ii) the FFP filtrate constitutes from 6% to 83% (and preferably 45.5%) of the combined volume of (a)-(c), and (iii) when the lysate, filtrate and heparin are combined with L-glutamine-containing, serum-free, low glucose medium suitable for mammalian cell growth, in order to form a cell growth medium wherein (i) the kit's contents constitute 3% to 25% (and preferably 11%) of the medium by volume and (ii) heparin is at a concentration of from 0 U/ml to 10 U/ml (and preferably 1 U/ml), the resulting cell growth medium permits the expansion of human CD34⁻ stem cells and the resulting expanded CD34⁻ stem cells retain the ability to differentiate.

This invention also provides a composition of matter comprising (a) human CD34⁻ stem cells and (b) any of the embodiments of the subject cell growth medium.

In the event that this composition of medium and stem cells is to be administered to a subject, as envisioned in this invention, it is preferred that the composition be immunocompatible with the patient's blood type. In this regard, several preferred embodiments exist in connection with the clinical use of the instant composition of matter. In the first, the platelet lysate is type O (universal donor), the FFP filtrate is type AB (universal donor), and the composition is administered to a patient having any blood type (i.e., O, A, B or AB). In the second preferred embodiment, the platelet lysate, the FFP filtrate and the patient all have the same blood type. In the third preferred embodiment, the FFP filtrate is type AB, and the platelet lysate type and patient type are the same and can be any blood type (e.g., FFP filtrate is type AB and the platelet lysate type and patient type are both O). Finally, if the patient is type O, the FFP used can be of any blood type. With regard to the Rh factor, it is preferred, but not necessary, that the patient type match that of the FFP filtrate and platelet lysate.

This invention further provides a method for making a human platelet lysate free of solid matter greater than 0.22 μm in diameter, comprising the following steps:
(i) freezing human platelet concentrate, thereby lysing the platelets therein;
(ii) thawing the resulting lysed platelets;
(iii) centrifuging the thawed lysed platelets at a speed and for a duration suitable to pellet solid matter therein;
(iv) re-centrifuging the supernatant from step (iii) at a speed and for a duration suitable to pellet solid matter therein; and
(v) filtering the supernatant from step (iv) at least twice using filters of decreasing pore size, wherein the first filtration is performed using a filter having pores of at least 5 μm, and the last filtration is performed using a filter having pores no larger than 0.22 μm.

In one embodiment of this invention, filtering step (v) is omitted.

This invention still further provides a method for making a human fresh frozen plasma (FFP) filtrate free of solid matter greater than 0.22 μm in diameter, comprising the following steps:
(i) thawing human FFP;
(ii) centrifuging the thawed FFP at a speed and for a duration suitable to separate the liquid and solid portions thereof; and
(iii) filtering the resulting liquid portion at least twice using filters of decreasing pore size, wherein the first filtration is performed using a filter having pores of at least 5 μm, and the last filtration is performed using a filter having pores no larger than 0.22 μm.

Alternatively, the FFP filtrate of part (b) of the cell growth medium is prepared according to the following steps: (i) thawing human FFP; (ii) freezing the thawed human FFP; (iii) thawing the human FFP from step (ii); and (iv) centrifuging the thawed FFP from step (iii) at a speed and for a duration suitable to separate the liquid and solid portions thereof.

During the preparation method of the FFP, the thawed FFP from step (iii) can be frozen and thawed at least once again before the centrifugation step (iv). In particular, the FFP can be frozen at a temperature of less than or equal to −35° C. and further can be thawed at temperatures of 5° C.±3° C. overnight, resulting in agglomeration of factors, which normally would lead to an agglutination of cultured MSCs.

In a further embodiment of this method of the invention, the centrifuging step can be done at 4000×g for at least 10 min. in order to precipitate the above mentioned agglomerated factors When using the thawing and freezing steps as described above a filtering step of the liquid portion resulting from the centrifugation step (iv) can be omitted. The doubling time of cultured MSCs in the medium prepared by using the FFP pretreated via the cryoprecipitate-removal step is comparable to the doubling time in the medium prepared via the filtering step of the FFP component.

This invention also provides a method for making a cell growth medium comprising the step of combining the following:
(a) a human platelet lysate free of solid matter greater than 0.22 μm in diameter, wherein the lysate constitutes from 2% to 15% (and preferably 6%) of the total volume of the cell growth medium;
(b) a human fresh frozen plasma (FFP) filtrate free of solid matter greater than 0.22 μm in diameter, wherein the FFP filtrate constitutes from 1% to 10% (and preferably 5%) of the total volume of the cell growth medium;
(c) heparin in an amount sufficient to yield a concentration of from 0 U/ml to 10 U/ml (and preferably 1 U/ml) of the cell growth medium; (d) L-glutamine in an amount sufficient to yield a concentration of from 0.5 mM to 10 mM; and (e) a serum-free, low glucose medium suitable for mammalian cell growth, wherein the serum-free, low glucose medium constitutes from 75% to 97% (and preferably 89%) of the total volume of the cell growth medium, and may contain the L-glutamine of part (d);

wherein the cell growth medium permits the expansion of human CD34$^-$ stem cells and wherein the resulting expanded CD34$^-$ stem cells retain the ability to differentiate.

This invention provides a method for expanding a population of human CD34$^-$ stem cells comprising the step of incubating the stem cells at a suitable temperature in the subject cell growth medium. Preferably, the suitable temperature is between 36 and 38° C., and preferably at 37° C.

This invention also provides a human CD34$^-$ stem cell (i) having the ability to differentiate, and (ii) resulting from an expansion of a population of human CD34$^-$ stem cells, wherein the expansion comprises incubating the population of stem cells at a suitable temperature in the subject cell growth medium.

Finally, this invention provides a population of human CD34$^-$ stem cells (i) having the ability to differentiate, and (ii) resulting from an expansion of a population of human CD34$^-$ stem cells, wherein the expansion comprises incubating the population of stem cells at a suitable temperature in the subject cell growth medium.

This invention will be better understood by reference to the Experimental Details which follow, but those skilled in the art will readily appreciate that the specific experiments detailed are only illustrative of the invention as described more fully in the claims which follow thereafter.

Experimental Details

A. Preparation and Use of Stem Cell-Related Materials

Fresh Frozen Plasma (Medicinal Product)

Fresh frozen plasma is a human plasma component used for transfusion or further fractionation processes and prepared by whole blood or by plasma collected by apheresis. FFP contains normal plasma levels of stable coagulation factors, albumin and immunoglobulins. Labile coagulation factors include Factor VIIIc.

Purity of FFP is achieved by collection via apheresis. Testing for HLA and HPA antibodies may be performed in individual donors to reduce the possible risk of allo-immunisation. ABO-compatible plasma is used (AB Rh+ as universal donor or ABO-matched).

FFP is used for the expansion of MSCs in a very low concentration during culture. To further decrease the risk of pathogen transmission, the donors for FFP are ideally tested for pathogens and are immunized against Hepatitis B. The risk for allo-immunisation of the patient and transmission of pathogens is reduced by the measures described.

Thrombocyte Lysate (Derived from Platelets: Medicinal Product)

The thrombocyte lysate is derived from platelets obtained by apheresis, ideally from a single donor. The platelet unit applied is free of contaminating erythrocytes and contains a very low number of leukocytes (<10$^5$/unit). The platelet lysate consists of cell-free lysate supporting the growth and purity of MSCs significantly. 1 ml of the lysate corresponds to $6.5 \times 10^8$-$2.0 \times 10^9$ platelets.

The possible risk of allo-immunisation is reduced by the use of leucocyte-poor single-donor apheresis products. Although the platelet-units do not contain erythrocytes (or contain only very low amounts), only O Rh+ platelets or matched units are used.

The possible risk of pathogen transmission is reduced by using single donor platelets, and testing for CMV. Further testing for pathogens such as Parvo B19, EBV or toxoplasmosis may be performed if desired.

B. Development and Testing of Bio-1 Composition (i.e., Media Containing Platelet Lysate and FFP Filtrate)

Cultivation of MSCs under the following conditions was compared: (a) IMDM+20% FBS as standard; (b) DMEM low glucose supplemented with 3% platelet lysate (=TK) and 5% FFP; and (c) DMEM low glucose supplemented with 6% platelet lysate (=TK) and 5% FFP.

MSC Proliferation Rate

The proliferation rates of MSCs from four donors were examined under the three chosen conditions. MSCs were cultured and passaged in the same initial density and the proliferation rate was determined during each passaging step.

Doubling time was calculated as $Td = t \log(2)/\log(q2/q1)$, where Td is doubling time, q1—initial cell amount, q2—final cell amount, t—duration of culture, days.

FIG. 1 shows the time required for one doubling of MSC under the three examined conditions. MSCs cultured in FBS-containing medium show a higher doubling time (2.86±0.43 days) than MSCs grown in DMEM+6% TK and 5% FFP (1.78±0.23 days). The growth speed of MSCs cultivated with less platelet lysate (DMEM+3% TK and 5% FFP) is intermediate between the two (2.4±0.32 days). This difference is statistically significant between IMDM+20% FBS and DMEM+6% TK and 5% FFP and a reproducible tendency is assessed when all three media were compared.

Figure 2:
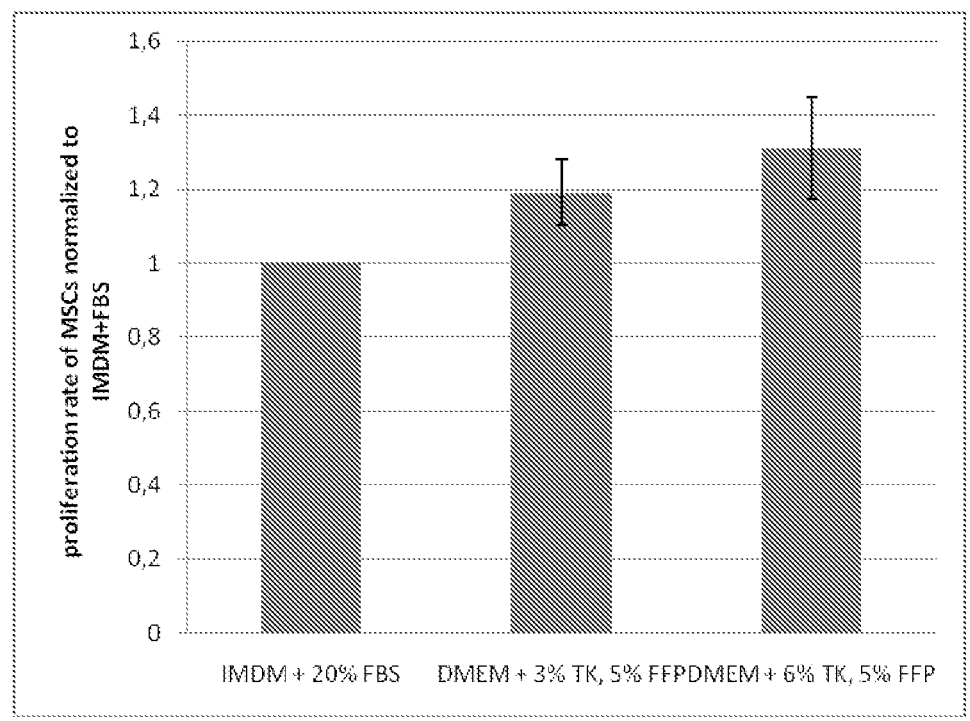
FIG. 2
Proliferation rate of MSC in different media.

Proliferation rate of MSCs in TK-containing media normalized to that in FBS-containing medium is represented in FIG. 2.

The medium composition DMEM+6% TK and 5% FFP (referred to as Bio-1) was chosen for further detailed analysis.

The expansion of MSCs in Bio-1 was studied over a prolonged cultivation period. Bone marrow cells were cultivated in Bio-1 (10 donors) or in IMDM+20% FBS (6 donors) and a pure MSC culture was obtained (confirmed by assays shown below). Cells were grown to reach confluency of 75%-85%, counted during passaging and re-plated in the same initial density. Cell doublings were calculated as t/Td, where t is duration of culture between passages (days) and Td is doubling time.

Figure 3:
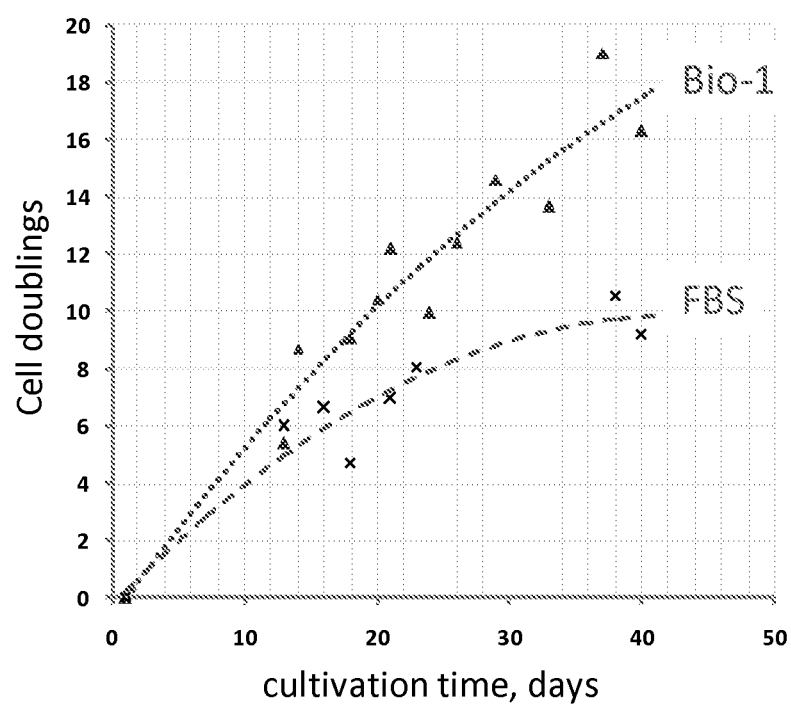
FIG. 3
Dynamics of MSC-growth in Bio-1.

Due to a great difference in the growth speed, MSCs grown in two media could not be passaged at the same time. Therefore, dynamics of MSC growth (FIG. 3) are presented as a trend line built over single data points representing the amount of cell doublings reached in a period of time between passages. Since the seeding was performed at low cell density, no further passaging steps after 45 days of cultivation were analysed because MSCs entered senescence (data not shown).

Characterisation of MSC-Specific Surface Markers in Different Media

Flow cytometric analysis of surface marker expression of MSCs grown under the above conditions was performed. A standard combination of markers, described as indicative of MSC phenotype and accepted as ISTH-criteria (Dominici, Le Blanc et al. 2006) was used. MSCs are known to lack the expression of hematopoietic markers CD34 and CD45, whereas CD73, CD90 and CD105 are highly expressed. The data obtained from the comparison of 5 donors are summarized in Table 3.

TABLE 3

| Surface markers | IMDM + 20% FBS | Bio-1 |
| --- | --- | --- |
| CD34 | 0.62 ± 0.82 | 0.20 ± 0.27 |
| CD45 | 0.38 ± 0.56 | 0.08 ± 0.03 |
| CD73 | 99.06 ± 1.59 | 99.87 ± 0.24 |
| CD90 | 94.17 ± 2.72 | 99.92 ± 0.05 |
| CD105 | 99.28 ± 1.07 | 99.83 ± 0.18 |

Figure 4:
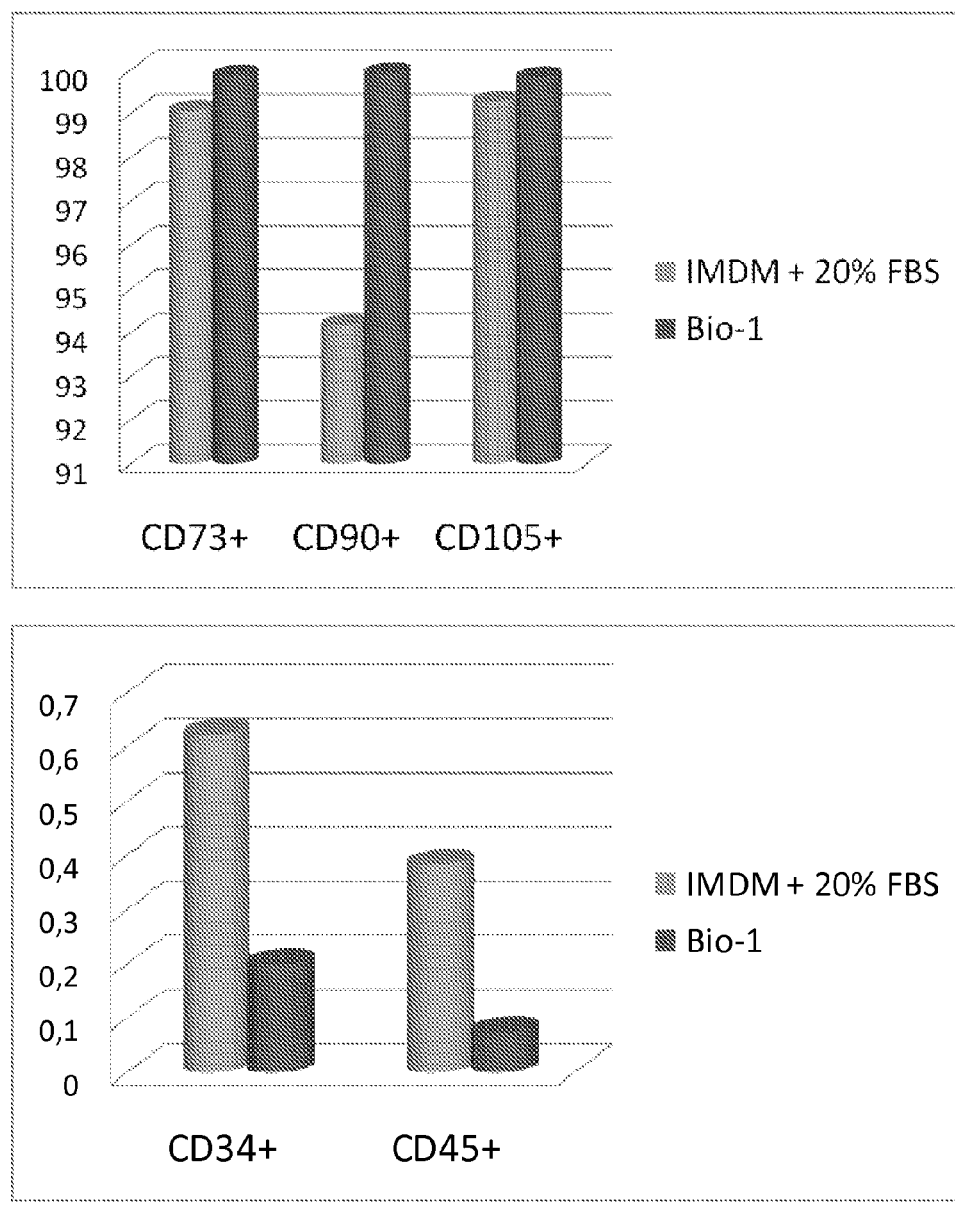
FIG. 4
Expression of MSC-specific surface proteins.

Cultivation in TK- and FFP-containing media clearly improved the phenotypic characteristics of obtained cultures. The trend was observed for expression of all analyzed markers (see FIG. 4).

Cell Viability and Morphology

Viability of MSC cultivated in Bio-1 was determined by 7-AAD staining in FACS analysis. The average viability calculated from analysis of MSCs from 11 donors was 97.61±1.26%.

Figure 5:
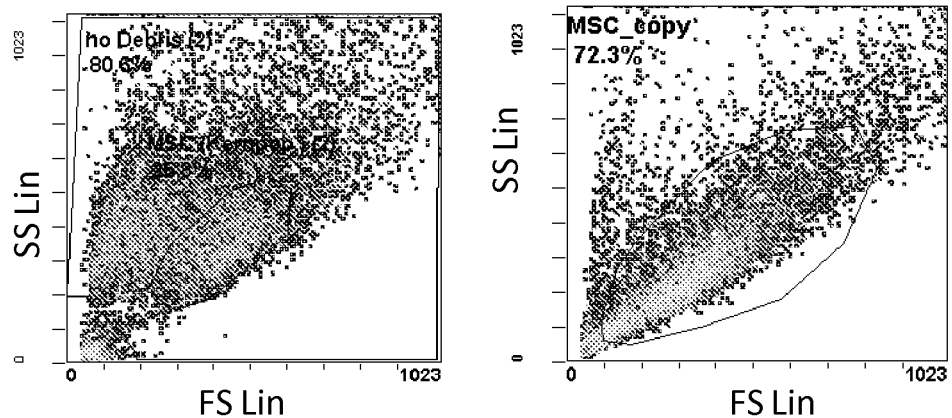
FIG. 5
Analysis of MSC population by flow cytometry. Left panel: MSCs cultivated in IMDM+20% FBS; right panel: MSCs cultivated in Bio-1.

Moreover, it appears that MSCs grown in Bio-1 represent a more homogenous cell population in terms of size and granularity, and are smaller in size when compared with MSCs cultivated in FBS-containing medium (see FIG. 5), which is regarded as a more physiological state of MSCs. This observation was confirmed by microscopic analysis (data not shown).

Functional Analysis of MSCs Grown in Bio-1

Figure 6:
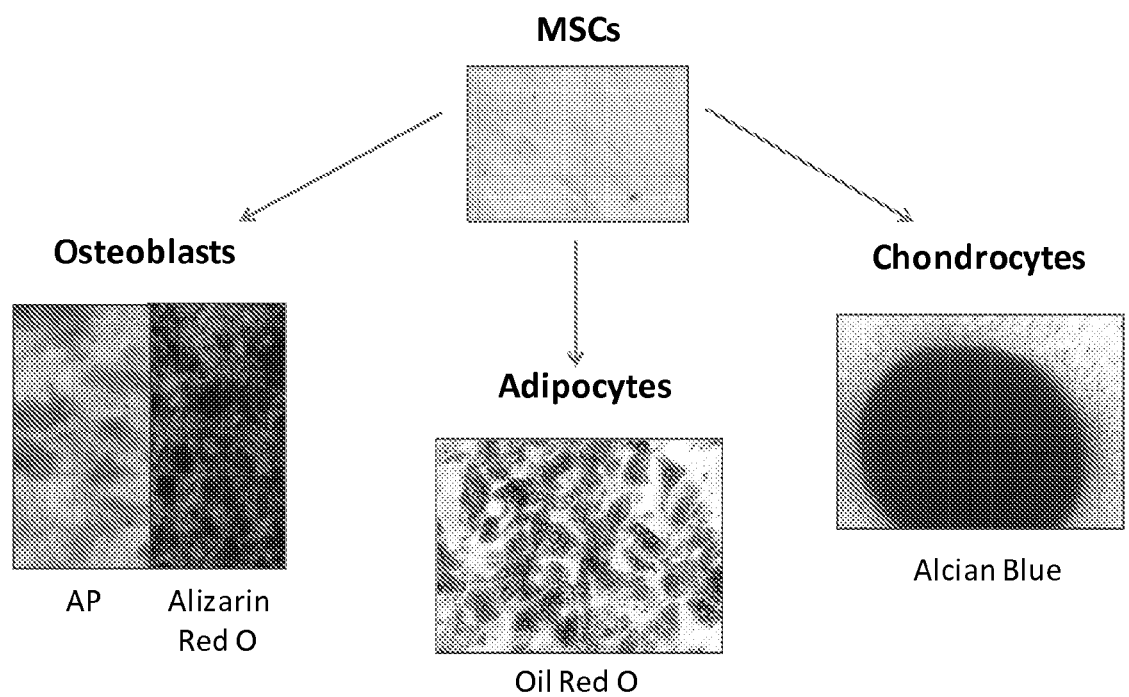
FIG. 6
Induced differentiation of MSC growth in Bio-1.

Clonogenicity of MSCs was proved in a CFU-F (fibroblast colony forming unit) assay (data not shown). Differentiation of MSCs toward adipogenic, osteogenic and chondrogenic lineages could be induced (see FIG. 6).

C. Further Development and Testing of Bio-1 Composition

In the following tests, preparation methods for two Bio-1 components, platelet lysate (TK) and fresh frozen plasma (FFP) were further improved. The purpose of the improvement was to remove from the medium all particles larger than 0.22 µm in size and obtain a clear solution without precipitates that can normally be seen in a medium having TK and FFP.

Starting components were prepared as follows:

Platelet lysate (TK) was obtained by freezing (−20° C. or −80° C.) and thawing of platelet concentrate, centrifuged at 10,000×g for 20' and at 4,000×g for 10' at 18° C. The resulting supernatant was used.

FFP was thawed out after storage at <−35° C.

In all experiments described below, the components were added to DMEM low glucose supplemented with L-glutamine and heparin in a concentration of 6% TK and 5% FFP.

In the first test, the medium was prepared as above and was passed through a 0.22 µm filter directly. MSCs of three donors were incubated in the filtered medium in a standard way. The cell growth was arrested and after two weeks of cultivation, the medium was exchanged to a non-filtered one, after which the cell growth resumed (data not shown).

In further tests, starting components were subjected to centrifugation and filtration steps separately and added to the medium afterwards. Visual analysis of medium clarity was performed (data not shown) and MSC growth rate was monitored.

Improvement of FFP Preparation

Figure 7:
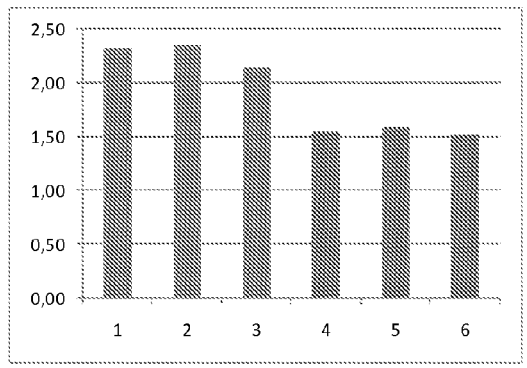
FIG. 7
Doubling time (days) of MSCs. Red (bars 4-6): doubling time of MSCs incubated with FFP filtered through at least 40 μm filter or filters with smaller pore size. Blue (bars 1-3): doubling time of MSCs incubated with FFP which was not filtered or was filtered through 100 μm only.
Figure 8:
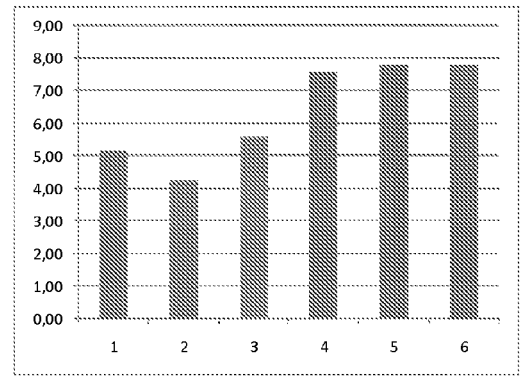
FIG. 8
Amount of doublings achieved after 12 days. Red (bars 4-6): doublings achieved by MSCs incubated with FFP filtered through at least 40 μm filter or filters with smaller pore size. Blue (bars 1-3): doublings achieved by MSCs incubated with FFP which was not filtered or was filtered through 100 μm only.
Figure 9:
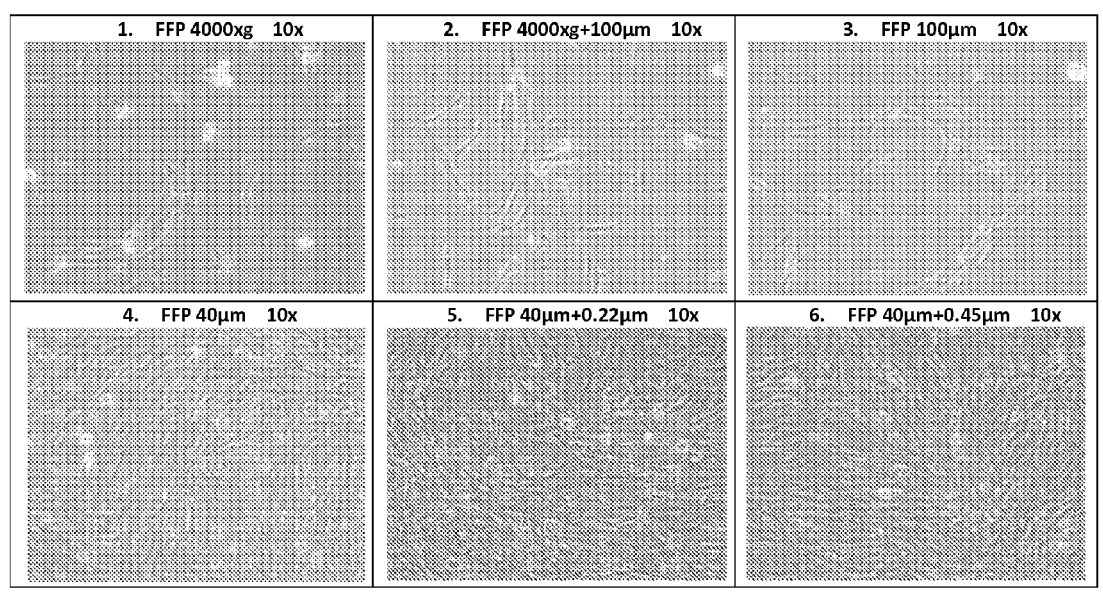
FIG. 9
Microscopic analysis was performed after 4 days of cultivation. Filtering of FFP through 40 μm, 40 μm or 0.22 μm filters significantly increased the growth rate of MSCs. The filtering through 100 μm alone improved the performance only slightly.

The method of TK preparation remained unchanged. FFP preparation was varied as followed:
1. FFP 4000×g
2. FFP 4000×g+100 µm
3. FFP 100 µm
4. FFP 40 µm
5. FFP 40 µm+0.22 µm
6. FFP 40 µm+0.45 µm Media were prepared and MSCs were incubated for 12 days. Cells grown in medium samples 4, 5 and 6 reached 85% confluency after 4 days and were re-passaged. MSCs were counted after trypsination and growth rate was estimated (FIGS. 7-9).

Improvement of TK Preparation

Figure 10:
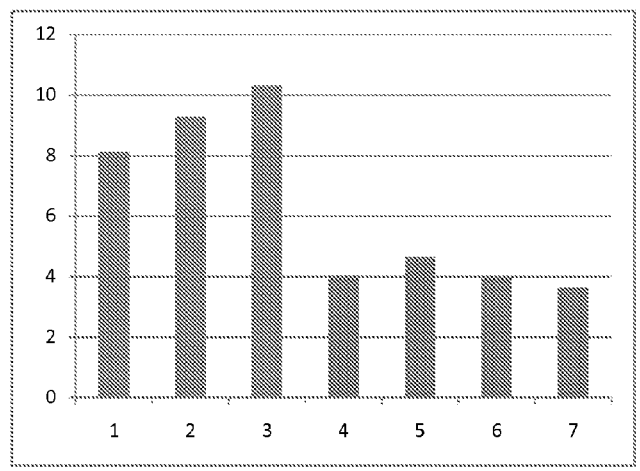
FIG. 10
Doubling time (days) of MSCs. Doubling time of MSCs cultivated in medium with FFP passed through 40 μm filter (red; bars 4-7) is about half that of MSCs incubated with unfiltered FFP (blue; bars 1-3).
Figure 11:
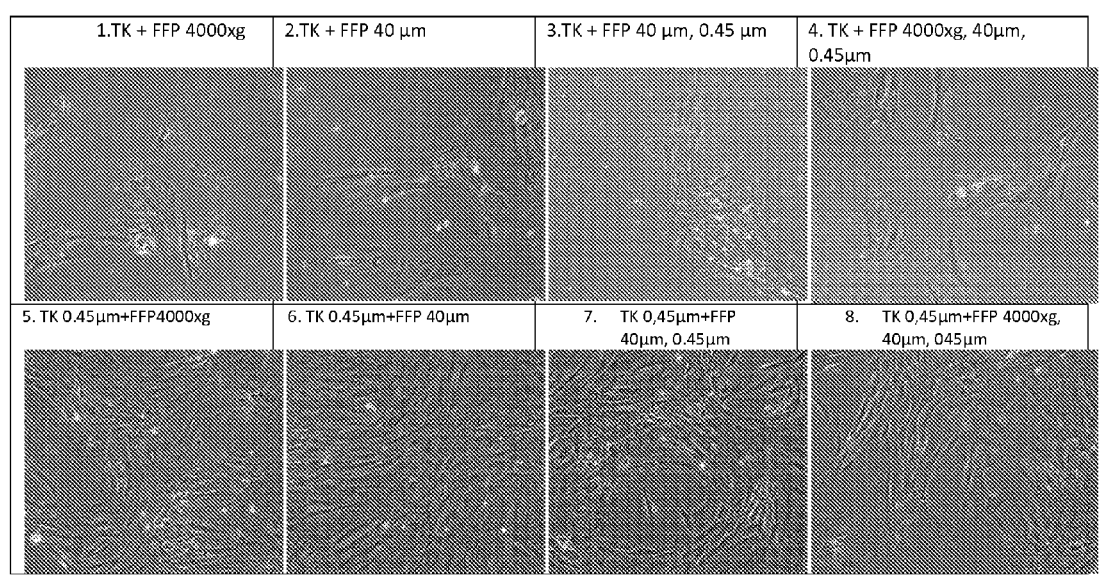
FIG. 11
Microscopic analysis after 9 days of cultivation. MSCs of late passages were used for this analysis, which explains a long doubling time and flattened morphology typical for senescent MSCs (pictures 1-4). However, incubation in medium with filtered FFP not only increased cell growth rate but also improved morphology of cells (pictures 5-8).
Figure 12:
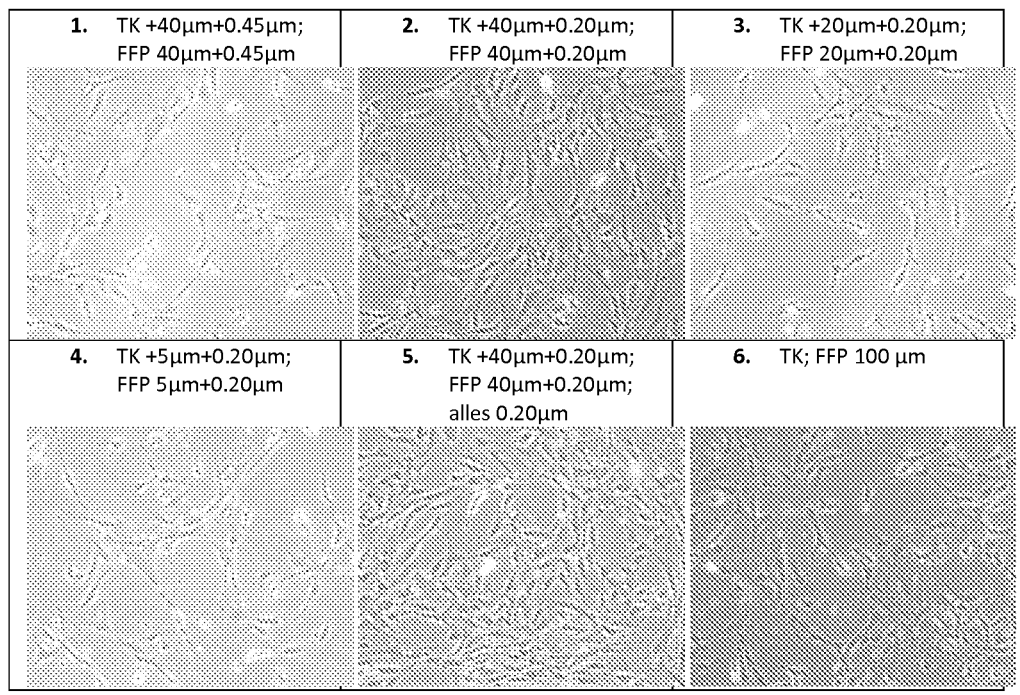
FIG. 12

Comparison between MSC growth in TK prepared in a conventional way and TK additionally passed though a 0.45 µm filter was performed. Preparations of FFP varied as indicated below. Doubling times of MSCs cultivated in these media were estimated and microscopic analysis was performed (FIGS. 10-12).

The effect of the TK filtration via smaller pores or combinations of different filters (8 µm, 0.8 µm and 0.2 µm) were tested. None of the tested combinations significantly changed the cell growth rate (data not shown). However, the resulting medium was macroscopically free of particles and more transparent, especially when 0.8 µm and 0.2 µm filters were used. Less aggregation was observed in cell suspension after trypsination of cells grown in filtered medium compared to the standard medium, due to the absence of sedimenting platelets.

Moreover, the efficiency of filtration can be monitored by flow cytometry of CD41$^+$ cells. In unfiltered TK, the remaining platelet membranes have the ability to anchor MSCs, which results in a CD41$^+$ signal. This signal is removed for the most part by filtration steps using small pores.

Figure 13:
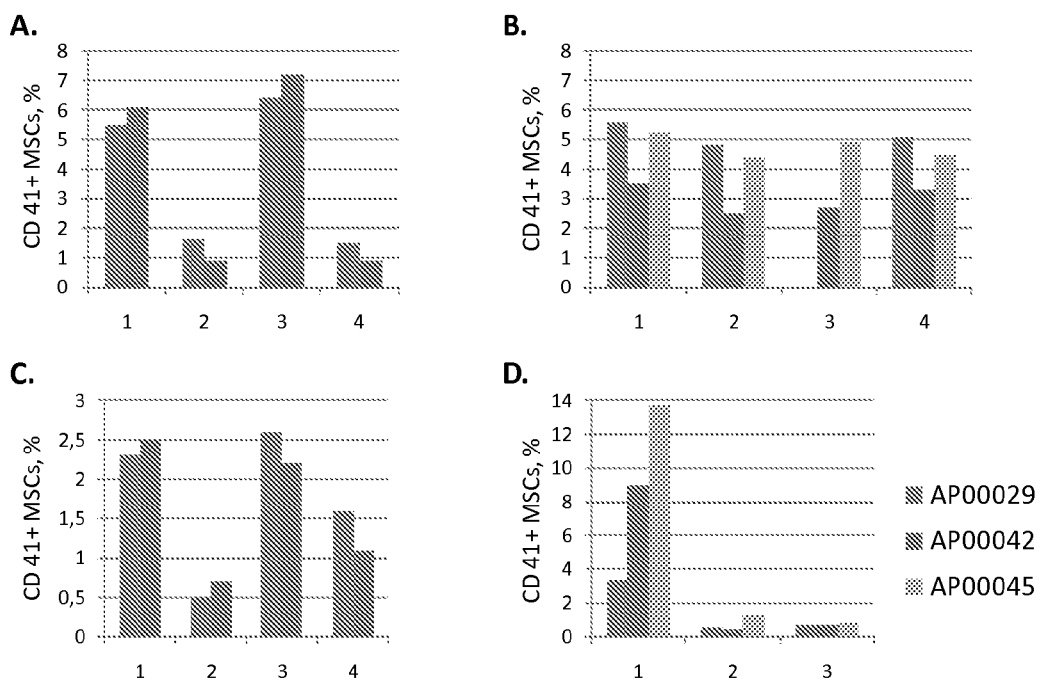

An example of this is presented in FIG. 13. Different filtration steps were performed with either TK or FFP or both (FIG. 13A-C). Subsequently, the resulting medium was submitted to filtration (FIG. 13D). It is pointed out that all studied medium variations sufficiently supported cell growth (data not shown). In all tests, the control was the standard Bio-1 prepared without additional filtration steps. Filtration of TK through 0.8 µm and 0.2 µm pores, alone or in combination with FFP filtration steps, resulted in a significant decrease of the CD41$^+$ signal (FIGS. 13A and C). Moreover, the level of this effect seemed dependent on the efficiency of filtration, as the subsequent filtration of TK through 0.8 µm and 0.2 µm resulted in a more pronounced CD41$^+$ decrease than did filtration through 0.2 µm pores alone (compare FIGS. 13C, 2 and 4). This is supported by the results presented in FIG. 13D. Filtration through 8 µm did not lead to a significant reduction of the CD41$^+$ signal and served solely to remove larger-sized particles and thus facilitate subsequent filtration through smaller pores. As expected, the filtration of FFP did not show any difference with regard to the CD41$^+$ signal.

Further Optimization: Modified FFP Preparation

Figure 14:
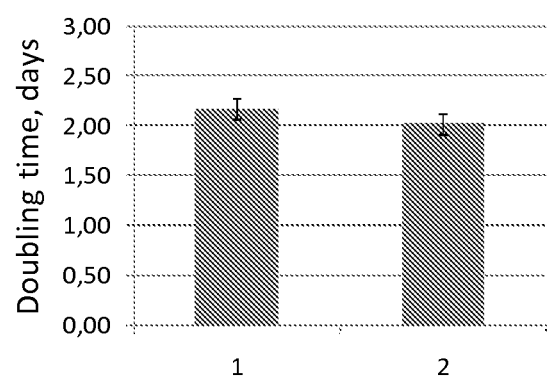

The purpose of the following step was to remove coagulating factors from FFP and prevent eventual clotting of medium and aggregation of cells as well as precipitation of platelet lysate residues. For this purpose, FFP was frozen at <−35° C. and thawed at 5±3° C. overnight. These steps were repeated one more time, followed by the centrifugation of the FFP at 4000×g for 10 min. The supernatant (cryoprecipitate-free FFP) was used for Bio-1 preparation. The comparison of MSC growth in a standard Bio-1 and in Bio-1 with cryoprecipitate-free FFP is presented in FIG. 14. The doubling times achieved by cells in both studied medium variations were comparable, with slightly improved growth in the cryoprecipitate-free FFP. This medium was also virtually free of contaminating particles so that no additional FFP filtration was needed.

Reconstitution of the Platelet Pellet in FFP with a Following Preparation of Bio-1 Medium Supplement In order to accomplish the maximum of blood group compatibility with regard to blood group antigens and isoagglutinins in plasma as described above and to exclude any eventual incompatibilities between the medium supplements, an additional step in the TK preparation may be necessary in some cases. This may play a role when the platelet concentrate is collected in autologous plasma containing isoagglutinins. The compatibility with regard to isoagglutinins of FFP and plasma of the thrombocyte concentrate must be considered.

For this, the platelets can be collected by centrifugation at 2000×g for 10' or 5000×g for 6' analogous to washed platelets. The pellet is collected and reconstituted in FFP (standard, filtered or cryoprecipitate-free) and frozen at ≤−20° C. Following preparation steps can be performed as described above for TK.

The supplement can be added to the basal medium (such as DMEM or α-MEM). The end volume of the supplement and the amount added to the basal medium can be adjusted depending on the desired end composition. For example, if 5% of platelet concentrate and 5% of FFP are chosen for optimal cell growth, 200 ml of platelets can be collected after centrifugation in a small volume and resuspended in 200 ml of FFP. The supplement produced this way can be added to the basal medium to the end concentration of 5%.

The following points are noted regarding the FFP and TK amounts referred to herein. 1% FFP in 1 l of Bio-1 corresponds to 8.0-10.0 ml of coagulatively active human plasma. Regarding the platelet lysate, the final concentration of platelet in the product and the percentage in Bio-1 depend on the method of platelet preparation used. (1) TK from apheresis (Apceth): 1 ml of TK-lysate corresponds to $6.5 \times 10^8$-$4.5 \times 10^9$ of platelets. Accordingly, 1 l of Bio-1 having 1% TK contains an amount of lysate equal to $6.5 \times 10^9$-$4.5 \times 10^{10}$ of platelets. The percentage of platelet lysate used for Bio-1 must be calculated based on the platelet amount in the starting material and the vol % values set forth in this application. (2) Platelet lysate from whole blood: there are $45$-$90 \times 10^9$ platelets in 50-60 ml suspension.

References

Blande, et al., "Adipose tissue mesenchymal stem cell expansion in animal serum-free medium supplemented with autologous human platelet lysate", *Transfusion*, Vol. 49, December 2009; 2680-2685.

Capelli, et al. (2007) "Human platelet lysate allows expansion and clinical grade production of mesenchymal stromal cells from small samples of bone marrow aspirates or marrow filter washouts." *Bone Marrow Transplant.* 40(8):785-91.

Horn et al. (2010). "Impact of individual platelet lysates on isolation and growth of human mesenchymal stromal cells" *Cytotherapy*, 12: 888-898.

Kocaoemer, et al., "Human AB serum and thrombin-activated platelet-rich plasma are suitable alternatives to fetal calf serum for the expansion of mesenchymal stem cells from adipose tissue", *Stem Cells*, Nov. 11, 2008; 1271-1278.

Langer and Gawaz, "Platelets in regenerative medicine", *Basic Res Cardiol* 103:299-307 (2008).

Muller, et al. (2006). "Animal serum-free culture conditions for isolation and expansion of multipotent mesenchymal stromal cells from human BM." *Cytotherapy* 8(5): 437-44.

Salvadè, et al., "Characterization of Platelet Lysate Cultured Mesenchymal Stromal Cells and Their Potential Use in Tissue-Engineered Osteogenic Devices for the Treatment of Bone Defects." *Tissue Eng Part C Methods.* 15, 2009:185-196.

Schallmoser, et al. (2008) "Rapid large-scale expansion of functional mesenchymal stem cells from unmanipulated bone marrow without animal serum." *Tissue Eng Part C Methods.* 14(3):185-96.

Stellos and Gawaz, "Platelet interaction with progenitor cells: Potential implications for regenerative medicine", *Thromb Haemost* 2007; 98:922-929.

What is claimed is:

1. A cell growth medium comprising (a) a human platelet lysate free of solid matter greater than 0.22 μm in diameter, wherein the lysate constitutes from 2% to 15% of the total volume of the cell growth medium; (b) a human fresh frozen plasma (FFP) filtrate free of solid matter greater than 0.22 μm in diameter, wherein the FFP filtrate constitutes from 1% to 10% of the total volume of the cell growth medium; (c) heparin at a concentration of from 0 U/ml to 10 U/ml of the cell growth medium; (d) L-glutamine at a concentration of from 0.5 mM to 10 mM; and (e) a serum-free, low glucose medium suitable for mammalian cell growth, wherein the serum-free, low glucose medium constitutes from 75% to 97% of the total volume of the cell growth medium, and may contain the L-glutamine of part (d); (i) wherein the FFP is the fluid portion of human blood that has been centrifuged, separated, and frozen solid within six hours of collection, (ii) wherein the cell growth medium permits the expansion of human CD34⁻ stem cells, and (iii) wherein the resulting expanded CD34⁻ stem cells retain the ability to differentiate.

2. The cell growth medium of claim 1, wherein the platelet lysate of part (a) is prepared according to the following steps: freezing human platelet concentrate, thereby lysing the platelets therein; (ii) thawing the resulting lysed platelets; (iii) centrifuging the thawed lysed platelets at a speed and for a duration suitable to pellet solid matter therein; (iv) re-centrifuging the supernatant from step (iii) at a speed and for a duration suitable to pellet solid matter therein; and (v) filtering the supernatant from step (iv) at least twice using filters of decreasing pore size, wherein the first filtration is performed using a filter having pores of at least 5 μm, and the last filtration is performed using a filter having pores no larger than 0.22 μm.

3. The cell growth medium of claim 2, wherein the human platelet concentrate of step (i) is prepared by: centrifuging platelets and thereby pelleting them; separating the pelleted platelets from the liquid phase; and reconstituting the resulting platelets in FFP.

4. The cell growth medium of claim 1, wherein the FFP filtrate of part (b) is prepared by: thawing human FFP; centrifuging the resulting thawed FFP at a speed and for a duration suitable to separate the liquid and solid portions thereof; and filtering the resulting liquid portion at least twice using filters of decreasing pore size, wherein the first filtration is performed using a filter having pores of at least 5 μm, and the last filtration is performed using a filter having pores no larger than 0.22 μm.

5. The cell growth medium of claim 1, wherein the FFP filtrate of part (b) is prepared by: (i) thawing human FFP; (ii) freezing the thawed human FFP; (iii) thawing the resulting human FFP; and (iv) centrifuging the resulting thawed FFP at a speed and for a duration suitable to separate the liquid and solid portions thereof.

6. The cell growth medium of claim 5, wherein the thawed FFP from step (iii) is frozen and thawed at least once again before the centrifugation step (iv).

7. The cell growth medium of claim 1, wherein the FFP filtrate of part (b) is prepared by: (i) thawing human FFP; (ii) freezing the thawed human FFP; (iii) thawing the resulting human FFP; and (iv) centrifuging the resulting thawed FFP at a speed and for a duration suitable to separate the liquid and solid portions thereof, wherein the liquid portion resulting from step (iv) is not filtered.

8. The cell growth medium of claim 1, wherein the cell growth medium is free of animal serum.

9. The cell growth medium of claim 1, wherein the platelet lysate and FFP filtrate are matched with respect to blood group antigens ABO and Rh.

10. A cell growth medium supplement comprising (a) human platelet lysate free of solid matter greater than 0.22 µm in diameter, wherein the lysate constitutes from 17% to 94% of the total volume of the cell growth medium supplement; and (b) human fresh frozen plasma (FFP) filtrate free of solid matter greater than 0.22 µm in diameter, wherein the FFP filtrate constitutes from 6% to 83% of the total volume of the cell growth medium supplement; wherein when the cell growth medium supplement is combined with heparin and an L-glutamine-containing, serum-free, low glucose medium suitable for mammalian cell growth, in order to form a cell growth medium containing (i) 3% to 25% by volume of the cell growth medium supplement, (ii) heparin at a concentration of from 0 U/ml to 10 U/ml, and (iii) L-glutamine at a concentration of from 0.5 mM to 10 mM, (i) wherein the FFP is the fluid portion of human blood that has been centrifuged, separated, and frozen solid within six hours of collection, (ii) wherein the resulting cell growth medium permits the expansion of human CD34⁻ stem cells, and (iii) wherein the resulting expanded CD34⁻ stem cells retain the ability to differentiate.

11. The cell growth medium supplement of claim 10, further comprising heparin, wherein when the cell growth medium supplement is combined with L-glutamine-containing, serum-free, low glucose medium suitable for mammalian cell growth, in order to form a cell growth medium containing 3% to 25% by volume of the cell growth medium supplement and having from 0 U/ml to 10 U/ml of heparin, the resulting cell growth medium permits the expansion of human CD34⁻ stem cells and the resulting expanded CD34⁻ stem cells retain the ability to differentiate.

12. The cell growth medium supplement of claim 10, wherein the platelet lysate of part (a) is prepared according to the following steps: freezing human platelet concentrate, thereby lysing the platelets therein; (ii) thawing the resulting lysed platelets;
(iii) centrifuging the thawed lysed platelets at a speed and for a duration suitable to pellet solid matter therein; (iv) re-centrifuging the supernatant from step (iii) at a speed and for a duration suitable to pellet solid matter therein; and (v) filtering the supernatant from step (iv) at least twice using filters of decreasing pore size, wherein the first filtration is performed using a filter having pores of at least 5 µm, and the last filtration is performed using a filter having pores no larger than 0.22 µm.

13. The cell growth medium supplement of claim 10, wherein the FFP filtrate of part (b) is prepared according to the following steps: (i) thawing human FFP;
(ii) centrifuging the thawed FFP at a speed and for a duration suitable to separate the liquid and solid portions thereof; and (iii) filtering the resulting liquid portion at least twice using filters of decreasing pore size, wherein the first filtration is performed using a filter having pores of at least 5 µm, and the last filtration is performed using a filter having pores no larger than 0.22 µm.

14. The cell growth medium supplement of claim 10, wherein the cell growth medium supplement is free of animal serum.

15. The cell growth medium supplement of claim 10, wherein the platelet lysate and FFP filtrate are matched with respect to blood group antigens ABO and Rh.

16. A human platelet lysate free of solid matter greater than 0.22 µm in diameter, wherein the platelet lysate is prepared according to the following steps: (i) freezing human platelet concentrate, thereby lysing the platelets therein; (ii) thawing the resulting lysed platelets; (iii) centrifuging the thawed lysed platelets at a speed and for a duration suitable to pellet solid matter therein; (iv) re-centrifuging the supernatant from step (iii) at a speed and for a duration suitable to pellet solid matter therein; and (v) filtering the supernatant from step (iv) at least twice using filters of decreasing pore size, wherein the first filtration is performed using a filter having pores of at least 5 µm, and the last filtration is performed using a filter having pores no larger than 0.22 µm.

17. A kit for use in expanding human CD34⁻ stem cells comprising, in separate compartments, (a) a human platelet lysate free of solid matter greater than 0.22 µm in diameter, and (b) a human fresh frozen plasma (FFP) filtrate free of solid matter greater than 0.22 µm in diameter, wherein (i) the lysate constitutes from 17% to 94% of the combined volume of (a) and (b), (ii) the FFP filtrate constitutes from 6% to 83% of the combined volume of (a) and (b), and (iii) when the lysate and filtrate are combined with heparin and with L-glutamine-containing, serum-free, low glucose medium suitable for mammalian cell growth, in order to form a cell growth medium wherein (i) the kit's contents constitute 3% to 25% of the medium by volume and (ii) heparin is at a concentration of from 0 U/ml to 10 U/ml, (i) wherein the FFP is the fluid portion of human blood that has been centrifuged, separated, and frozen solid within six hours of collection, (ii) wherein the resulting cell growth medium permits the expansion of human CD34⁻ stem cells, and (iii) the resulting expanded CD34⁻ stem cells retain the ability to differentiate.

18. The kit of claim 17 comprising, in separate compartments, (a) a human platelet lysate free of solid matter greater than 0.22 µm in diameter, (b) a human fresh frozen plasma (FFP) filtrate free of solid matter greater than 0.22 µm in diameter, and (c) heparin, wherein (i) the lysate constitutes from 17% to 94% of the combined volume of (a)-(c), (ii) the FFP filtrate constitutes from 6% to 83% of the combined volume of (a)-(c), and (iii) when the lysate, filtrate and heparin are combined with L-glutamine-containing, serum-free, low glucose medium suitable for mammalian cell growth, in order to form a cell growth medium wherein (i) the kit's contents constitute 3% to 25% of the medium by volume and (ii) heparin is at a concentration of from 0 U/ml to 10 U/ml, the resulting cell growth medium permits the expansion of human CD34⁻ stem cells and the resulting expanded CD34⁻ stem cells retain the ability to differentiate.

19. A method for making a cell growth medium comprising the step of combining the following: (a) a human platelet lysate free of solid matter greater than 0.22 µm in diameter, wherein the lysate constitutes from 2% to 15% of the total volume of the cell growth medium; (b) a human fresh frozen plasma (FFP) filtrate free of solid matter greater than 0.22 µm in diameter, wherein the FFP filtrate constitutes from 1% to 10% of the total volume of the cell growth medium; (c) heparin in an amount sufficient to yield a concentration of from 0 U/ml to 10 U/ml of the cell growth medium; (d) L-glutamine in an amount sufficient to yield a concentration of from 0.5 mM to 10mM; and (e) a serum-free, low glucose medium suitable for mammalian cell growth, wherein the serum-free, low glucose medium constitutes from 75% to 97% of the total volume of the cell growth medium, and may contain the L-glutamine of part (d); (i) wherein the FFP is the fluid portion of human blood that has been centrifuged, separated, and frozen solid within six hours of collection, (ii) wherein the cell growth medium permits the expansion of human CD34⁻ stem cells, and (iii) wherein the resulting expanded CD34⁻ stem cells retain the ability to differentiate.

* * * * *